United States Patent [19]

Lantzsch

[11] 4,217,300
[45] Aug. 12, 1980

[54] PREPARATION OF DIHALOGENOVINYLCYCLOPROPANECARBOXYLIC ACIDS AND ESTERS

[75] Inventor: Reinhard Lantzsch, Cologne, Fed. Rep. of Germany

[73] Assignee: Bayer Aktiengesellschaft, Leverkusen, Fed. Rep. of Germany

[21] Appl. No.: 879,424

[22] Filed: Feb. 21, 1978

[30] Foreign Application Priority Data

Mar. 9, 1977 [DE] Fed. Rep. of Germany ....... 2710174

[51] Int. Cl.² ............................................. C07C 69/74
[52] U.S. Cl. ........................... 260/465 D; 260/346.22; 260/347.4; 549/60; 549/79; 560/124; 560/219
[58] Field of Search .............................. 560/124, 219; 260/346.22, 347.4, 332.2 R, 465 D

[56] References Cited

U.S. PATENT DOCUMENTS

| | | | |
|---|---|---|---|
| 3,077,496 | 2/1963 | Julia | 560/124 |
| 3,123,629 | 3/1964 | Julia | 560/124 |
| 3,652,652 | 3/1972 | Julia | 560/124 |
| 4,083,855 | 4/1978 | Itaya | 560/124 |
| 4,113,968 | 9/1978 | Mori | 560/124 |

FOREIGN PATENT DOCUMENTS

| | | | |
|---|---|---|---|
| 1356949 | 2/1964 | France | 560/124 |
| 7605172 | 11/1976 | Netherlands | 560/124 |

Primary Examiner—Norman Morgenstern
Assistant Examiner—Michael Shippen
Attorney, Agent, or Firm—Sprung, Felfe, Horn, Lynch & Kramer

[57] ABSTRACT

A process for the preparation of a dihalogenovinylcyclopropanecarboxylic acid or an ester thereof, of the formula

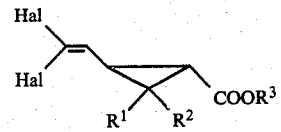

in which
Hal each independently is fluorine, chlorine or bromine,
$R^1$ and $R^2$ each independently is hydrogen or $C_{1-4}$-alkyl, or $R^1$ and $R^2$ together with the adjacent carbon atoms form a cycloaliphatic ring with up to 7 carbon atoms, and
$R^3$ is hydrogen, $C_{1-4}$-alkyl or optionally substituted arylmethyl or hetero-arylmethyl, which comprises reacting a 3-chloro-2-(2',2'-dihalovinyl)-propanecarboxylic acid ester of the formula

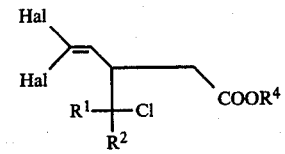

in which
$R^4$ is $C_{1-4}$-alkyl or optionally substituted arylmethyl or hetero-arylmethyl, with a base. The propane carboxylic acid esters are new and may be formed in situ by reacting a 3-(2',2'-dihalovinyl)-γ-butyrolactone of the formula

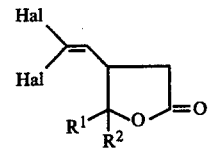

with a chlorinating agent and then with an alcohol of the formula $R^4$—OH. The end products are insecticidally active and can also be used as intermediates for producing other insecticides.

13 Claims, No Drawings

PREPARATION OF DIHALOGENOVINYLCYCLOPROPANECARBOXYLIC ACIDS AND ESTERS

The present invention relates to processes for the preparation of certain dihalogenovinyl-cyclopropanecarboxylic acids and their esters, which can be used as intermediate products for the synthesis of insecticides, or which have insecticidal properties.

It has already been disclosed to split 3-dimethylvinyl-substituted γ-lactones by reaction with thionyl chloride in the presence of alcohol and to cyclize the open-chain ester formed, by splitting off hydrogen halide under the action of alcoholates, to form the corresponding dimethylvinyl-substituted cyclopropanecarboxylic acid esters (see U.S. Pat. No. 3,077,496). However, the yields are unsatisfactory and bases which are not customary in industry and which are difficult to handle on a large scale, such as sodium tert.-amylate or sodium hydride in DMF, must be used. In addition, the reaction must be carried out in the anhydrous state and with dried solvents.

The present invention now provides a process for the preparation of a dihalogenovinyl-cyclopropanecarboxylic acid, or an ester thereof, of the general formula

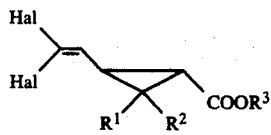

(I), in which
Hal represents fluorine, chlorine or bromine, the Hal atoms being identical or different,
$R^1$ and $R^2$, which may be identical or different, each represent hydrogen or $C_{1-4}$-alkyl, or $R^1$ and $R^2$ together with the adjacent carbon atom, form a cyclo-aliphatic ring with up to 7 carbon atoms and
$R^3$ represents hydrogen, $C_{1-4}$-alkyl or optionally substituted arylmethyl or hetero-arylmethyl,
in which (a) a compound of the general formula

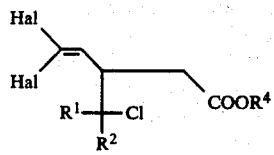

(II), in which
Hal, $R^1$ and $R^2$ have the meanings stated above, and $R^4$ represents $C_{1-4}$-alkyl or optionally substituted arylmethyl or hetero-arylmethyl,
is dehydrohalogenated in the presence of an aqueous base and optionally in the presence of a catalyst, or
(b) a compound of the general formula

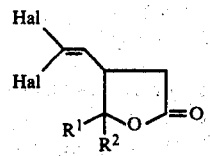

(III), in which
Hal, $R^1$ and $R^2$ have the meanings stated above, is reacted successively with a chlorinating agent and an alcohol of the general formula $$R^4\text{—OH} \qquad (IV),$$

in which
$R^4$ has the meaning stated above, and the resulting compound of the general formula (II) is reacted, without being isolated, with an aqueous base, optionally in the presence of a catalyst.

Furthermore, the invention also provides, as new compounds, the compounds of the general formula (II) in which Hal, $R^1$, $R^2$, $R^3$ and $R^4$ have the meanings stated above.

Furthermore, the present invention also provides a process for the preparation of a compound of the general formula (II), in which a compound of the general formula (III), in which Hal, $R^1$ and $R^2$ have the meanings stated above, is reacted successively with a chlorinating agent and an alcohol of the general formula (IV), in which $R^4$ has the meaning stated above.

Preferably, in the above formulae, $R^1$ and $R^2$ each represent $C_{1-4}$-alkyl (especially methyl), Hal represents chlorine or bromine, and $R^3$ and $R^4$ represents a benzyl, α- or β-naphthylmethyl, furylmethyl or benzofurylmethyl radical, which is optionally substituted in the aromatic ring or at the α-carbon atom by halogen (for example fluorine, chlorine or bromine), CN, alkyl with 1–4 carbon atoms, halogenoalkyl with 1–4 carbon atoms and 1–5 halogen atoms (for example trichloromethyl, trifluoromethyl or pentafluoroethyl), aryl (for example phenyl), hetero-aryl (for example thienyl or furyl) or aryloxy (for example phenoxy) which is itself optionally substituted by halogen, or halogenoalkoxy or halogenoalkylmercapto with, in each case, 1–4 carbon atoms and up to 5 halogen atoms.

The course of the dehydrohalogenation, according to the invention, of the compounds of the general formula (II) was surprising. Thus, it could not be expected that when the process is carried out with aqueous bases virtually no saponification of the ester group occurs, which, as is indeed known, proceeds under very mild conditions in an alkaline medium. In addition, it was surprising that virtually no elimination according to the equation which follows takes place under the process conditions according to the invention.

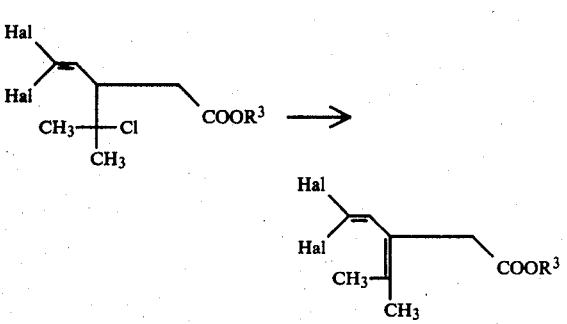

The advantage of the process according to the invention is that the cyclopropanecarboxylic acid derivatives of the general formula (I) can be obtained, in good purity, under conditions which are not very expensive industrially.

If 3-methyl-3-chloro-2-(2',2'-dichlorovinyl)-butanecarboxylic acid ethyl ester is used as the starting material, the course of the reaction can be represented by the following equation:

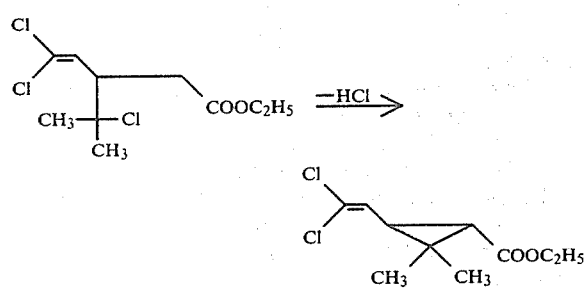

The process variant (a) is, in general, carried out at temperatures from about −20° to 120° C., preferably from about 0° to 100° C. The process is preferably carried out under normal pressure. In general, it is carried out in the diluent which was used in the preparation of the compound of the formula (II). However, other diluents can also be used, such as hydrocarbons, for example benzene, toluene or xylene, chlorohydrocarbons, such as chlorobenzene, or ethers. Quite generally, all the inert solvents which are not water-miscible can be used.

The reaction is carried out in the presence of an aqueous base, preferably NaOH or KOH. The process according to the invention is preferably carried out in a two-phase system consisting of water and a solvent which is not water-miscible. A catalyst is in general used that has the general formula

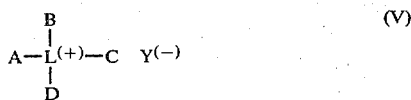 (V)

in which

L represents nitrogen or phosphorus,

A, B, C and D, independently of one another, each represent optionally substituted alkyl, aralkyl or aryl, or two of A, B, C and D that are adjacent, together with the central atom L and optionally one or more further hetero-atoms, form a heterocyclic ring, and $Y^{(-)}$ represents a halide, bisulphate or hydroxyl ion.

Catalysts of the general formula (V) have been described in the literature; the catalysts can all be prepared by known processes (Houben-Weyl, Volume XI, 2 page 587 et seq., Georg-Thieme-Verlag, Stuttgart 1958).

Catalysts of the general formula (V) in which A, B, C and D each represent alkyl with 1–18 carbon atoms (especially methyl, ethyl, propyl, butyl, hexyl, dodecyl or octadecyl), benzyl (which is optionally substituted by $C_1$–$C_4$-alkyl, methoxy or halogen) or phenyl (which is optionally substituted by $C_1$–$C_4$-alkyl, $C_1$–$C_4$-alkoxy or halogen), are preferred.

Particularly preferred catalysts of the formula (V) to be used in the process according to the invention are: tetraethylammonium chloride, tetrabutylammonium chloride, tetrabutylammonium bromide, tetrabutylphosphonium chloride, benzyltriethylammonium chloride, phenylbenzyldimethylammonium chloride, benzyldodecyldimethylammonium chloride and benzyltributylammonium chloride.

The amount of catalyst can vary within wide limits. In general, 0.1–10% by weight, preferably 0.3 to 6% by weight, relative to the weight of the compound of the general formula (II) employed, have proved suitable. The reaction is best carried out by adding the base either in the solid form or dropwise, in the form of an aqueous solution. The concentration of the aqueous solution of the base should be from about 10 to 50%. However, higher concentrations can also be used.

As already mentioned, the compounds of the general formula (II) are obtained by reacting a γ-butyrolactone of the general formula (III) with a chlorinating agent and an alcohol of the general formula (IV).

When 3-(2',2'-dichlorovinyl)-4-methyl-γ-valerolactone is used, the course of the reaction can be represented by the following equation:

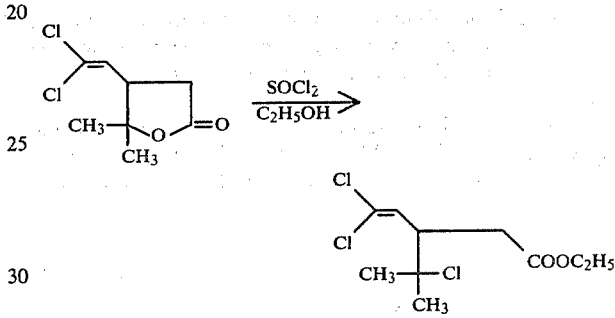

Alcohols of the formula (IV) in which $R^4$ represents 3-phenoxybenzyl, 3-phenoxy-α-cyanobenzyl or pentahalogenobenzyl, are particularly preferred. 3-Phenoxy-benzyl alcohol may be mentioned in particular.

Preferred chlorinating agents are thionyl chloride or phosgene.

The chlorination reaction is, in general, carried out at temperatures from about 50° to 150° C., preferably from about 70° to 110° C.

Suitable solvents are, in principle, all the solvents which boil in the temperature range indicated and do not react with the chlorinating agent.

Solvents which can be used are hydrocarbons, such as benzene, toluene or xylene, chlorohydrocarbons, such as chlorobenzene, or ethers, such as diisopropyl ether or dimethoxyethane. However, the reaction can also be carried out without a solvent, for example in an excess of thionyl chloride.

The reaction is carried out by heating the γ-lactone of the formula (III) and the chlorinating agent to the desired reaction temperature in a solvent or, if appropriate, in excess thionyl chloride, the mixture is then allowed to cool and the desired alcohol is added at a temperature between about 0° and 80° C., preferably between about 20° and 50° C. The excess thionyl chloride, if used, can optionally first be distilled off, in particular if a valuable alcohol is used. The ester formation can optionally be accelerated by adding an auxiliary base, such as a tertiary amine, for example triethylamine or pyridine.

The end of the reaction is best detected by IR spectroscopy, by the appearance of the ester-carbonyl band at about 1,720–1,740 $cm^{-1}$. If appropriate, the excess alcohol is then removed *in vacuo*, and the compounds of the general formula (II) are isolated by distillation or crystallization.

Preferably, however, the solution of the compound (II), for example in one of the solvents indicated above, is further reacted directly with a base, in accordance with process variant (b).

A particular advantage of the process according to the invention is that (in the case where $R_1=R_2=CH_3$ and Hal=Cl) the trans esters, which have a higher insecticidal action, are very predominantly formed. The cis proportion is, in each case, only about 5–10%.

The compounds of the formula (I), prepared in accordance with the present invention, can be used to combat insect pests. Such pests include:

from the order of the Thysanura, for example *Lepisma saccharina;* from the order of the Collembola, for example *Onychiurus armatus;* from the order of the Orthoptera, for example *Blatta orientalis, Periplaneta americana, Leucophaea madera, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., i Laphygma exigua, Mamestra brassicae, Panolis flammea, Prodenia litura, Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus sp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

An emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The present invention also provides an insecticidal composition containing as active ingredient a compound of the present invention in admixture with a solid or liquefied gaseous diluent or carrier or in admixture with a liquid diluent or carrier containing a surface-active agent.

The present invention also provides a method of combating insects which comprises applying to the insects, or to a habitat thereof, a compound of the present invention alone or in the form of a composition containing as active ingredient a compound of the present invention in admixture with a diluent or carrier. The following examples illustrate the process of the invention:

EXAMPLE 1

209 g of 4-methyl-3-(2′,2′-dichlorovinyl)-γ-valerolactone were dissolved in 800 ml of toluene, and 250 ml of thionyl chloride were added. The mixture was heated to 75°–80° C. for 6 hours and thereafter a further 250 ml of thionyl chloride were added. The mixture was again heated to 75°–80° C. for 6 hours and was allowed to cool; 400 ml of ethanol saturated with HCl were added dropwise at room temperature. The mixture was subsequently stirred for 8 hours at room temperature and ethanol and the majority of the toluene were distilled off. This crude solution contained, according to analysis by gas chromatography, 207 g (87% of theory) of 3-methyl-3-chloro-2-(2′,2′-dichlorovinyl)-butanecarboxylic acid ethyl ester

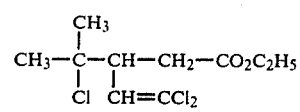

and was employed directly in the next stage in Examples 2–4. A sample was fractionally distilled over a column. The 3-methyl-3-chloro-2-(2′,2′-dichlorovinyl)-butanecarboxylic acid ethyl ester had a boiling point=91° C./0.3 mm Hg. $n_{20}^D = 1.4810$.

EXAMPLE 2

27.35 g of 3-methyl-3-chloro-2-(2′,2′-dichlorovinyl)-butanecarboxylic acid ethyl ester in the form of the crude solution prepared in Example 1 were dissolved in 50 ml of toluene. 3 g of tetrabutylammonium chloride were added and 16.8 g of 50% strength potassium hydroxide solution were then added dropwise at 25° C. The mixture was subsequently stirred for 3 hours, ice-water was added and the mixture was rendered neutral. After the toluene phase had been separated off, it was subjected to fractional distillation. 10.4 g of 2,2-dimethyl-3-(2′,2′-dichlorovinyl)-cyclopropanecarboxylic acid ethyl ester and 13.35 g of starting substance were recovered. This corresponded to a yield of 91%, relative to the 3-methyl-3-chloro-2-(2′,2′-dichlorovinyl)-butanecarboxylic acid ethyl ester reacted.

EXAMPLE 3

27.35 g of 3-methyl-3-chloro-2-(2′,2′-dichlorovinyl)-butanecarboxylic acid ethyl ester in the form of the crude solution prepared in Example 1 were dissolved in 50 ml of toluene. 2.5 g of tetrabutylammonium bromide were added and 11.2 g of 50% strength potassium hydroxide solution were then added dropwise at 40° C. After the dropwise addition had ended, the mixture was subsequently stirred for a further 4 hours at room temperature, the aqueous phase was rendered neutral and the toluene phase was separated off. The toluene phase was then subjected to fractional distillation. This gave 21.2 g (89.5% of theory) of 2,2-dimethyl-3-(2′,2′-dichlorovinyl)-cyclopropanecarboxylic acid ethyl ester, which was saponified to give the free acid, for example according to Coll. Czech. Chem. Comm. 24, page 2,234.

EXAMPLE 4

27.35 g of 3-methyl-3-chloro-2-(2′,2′-dichlorovinyl)-butanecarboxylic acid ethyl ester in the form of the crude solution prepared in Example 1 were dissolved in 50 ml of toluene. 2 g of tetrabutylphosphonium chloride were added and 16.8 g of 50% strength potassium hydroxide solution were then added dropwise at 0° C. The solution was subsequently stirred until it had reached room temperature and was then stirred for a further 1 hour at 35° C. It was then diluted with ice-water and rendered neutral and the organic phase was separated off and fractionated. This gave 21.9 g (92.5% of theory) of 2,2-dimethyl-3-(2′,2′-dichlorovinyl)-cyclopropanecarboxylic acid ethyl ester.

EXAMPLE 5

29.8 g of 4-methyl-3-(2′,2′-dibromovinyl)-γ-valerolactone were dissolved in 100 ml of toluene, and 25 ml of thionyl chloride were added. The mixture was heated to 75°–80° C. for 6 hours and thereafter a further 25 ml of thionyl chloride were added. The mixture was again heated to 75°–80° C. for 6 hours and was allowed to cool and 200 ml of ethanol saturated with HCl were added dropwise at room temperature. The mixture was subsequently stirred for 8 hours at room temperature and the ethanol (and some of the toluene) was distilled off in vacuo. 2 g of tetrabutylammonium bromide were added to this solution and 11.2 g of 50% strength potassium hydroxide solution were then added dropwise at 35° C. The mixture was stirred for a further 4 hours at room temperature and diluted with ice-water, the aqueous phase was rendered neutral and the toluene phase was separated off. The toluene phase was then subjected to fractional distillation. This gave 18.5 g of 2,2-dimethyl-3-(2',2'-dibromovinyl)-cyclopropanecarboxylic acid ethyl ester of boiling point 100°–103° C./0.1 mm Hg.

The ester was heated to 100° C. with 80 ml of glacial acetic acid and 15 ml of 20% strength hydrochloric acid for 4 hours. After cooling, the mixture was poured onto 250 ml of water, extracted by shaking with petroleum ether, dried with $Na_2SO_4$ and evaporated in a rotary evaporator. The residue was taken up in 150 ml of 1 N NaOH and the solution was extracted by shaking 3 times with methylene chloride. The aqueous phase was acidified at 0° C. with concentrated HCl and then extracted with methylene chloride. After drying with sodium sulphate, the methylene chloride was distilled off. The residue consisted of 2,2-dimethyl-3-(2',2'-dibromovinyl)-cyclopropanecarboxylic acid of melting point 110° C.

EXAMPLE 6

20.9 g of 4-methyl-3-(2',2'-dichlorovinyl)-γ-valerolactone were dissolved in 80 ml of toluene. After adding 20 ml of thionyl chloride, the mixture was heated to the boil for 12 hours. After cooling 22 g of 3-phenoxybenzyl alcohol were added dropwise, and 3 g of tetrabutylphosphonium chloride were added. 30 g of 50% strength potassium hydroxide solution were then added dropwise at room temperature. The mixture was subsequently stirred for 2 hours at room temperature, ice-water was added and it was rendered neutral. After separating off the toluene phase, the toluene was distilled off and the residue was purified on silica gel, using benzene as the running agent. This gave a product which consisted to the extent of 95% of trans-2,2-dimethyl-3-(2',2'-dichlorovinyl)-cyclopropanecarboxylic acid 3-phenoxybenzyl ester ($n_{20}{}^D = 1.5616$).

EXAMPLE 7

20.9 g of 4-methyl-3-(2',2'-dichlorovinyl)-γ-valerolactone were dissolved in 80 ml of toluene. After adding 20 ml of thionyl chloride, the mixture was heated to the boil for 12 hours and allowed to cool. After distilling off the excess thionyl chloride in vacuo, 20 g of 3-phenoxybenzyl alcohol were added dropwise and 5 g of tetrabutylammonium chloride were added. 30 g of 50% strength potassium hydroxide solution were then added dropwise at 40°–50° C. in the course of 30 minutes. The mixture was subsequently stirred for 12 hours, ice-water was added and it was rendered neutral. After separating off the toluene phase, the toluene was distilled off and the residue was purified on silica gel, using benzene as the running agent. This gave a product which consisted to the extent of 85–90% of trans-2,2-dimethyl-3-(2',2'-dichlorovinyl)-cyclopropanecarboxylic acid 3-phenoxybenzyl ester ($n_{20}{}^D = 1.5624$).

It will be appreciated that the instant specification and examples are set forth by way of illustration and not limitation, and that various modifications and changes may be made without departing from the spirit and scope of the present invention.

What we claim is:

1. A process for the preparation of a dihalogenovinyl-cyclopropanecarboxylic acid or an ester thereof, of the general formula

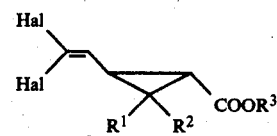

in which

Hal each independently is fluorine, chlorine, or bromine, $R^1$ and $R^2$ each independently is hydrogen or $C_{1-4}$-alkyl, or $R^1$ and $R^2$ together with the adjacent carbon atom form a cycloaliphatic ring with up to 7 carbon atoms, and $R^3$ is hydrogen, $C_{1-4}$-alkyl or arylmethyl or heteroarylmethyl, which comprises reacting a 3-chloro-2-(2',2'-dihalovinyl)-butane carboxylic acid ester of the formula

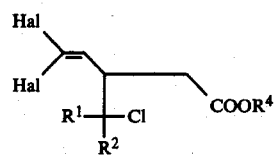

in which $R^4$ is $C_{1-4}$-alkyl or arylmethyl or hetero-arylmethyl, with a base in aqueous solution in the presence of an inert solvent selected from the group consisting of a hydrocarbon, chlorohydro-carbon or ether, and in the presence of a catalyst of the formula

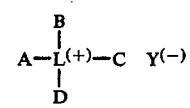

in which

L is nitrogen or phosphorus,

A, B, C, and D each independently is alkyl, aralkyl or aryl, or two of A, B, C and D together with the central atom L and optionally at least one further hetero-atom form a heterocyclic ring, and $Y^{(-)}$ is a halide, bisulphate or hydroxyl ion.

2. A process according to claim 1, wherein the butane carboxylic acid ester is formed in situ by reacting a 3-(2',2'-dihalovinyl)-γ-butyrolactone of the formula

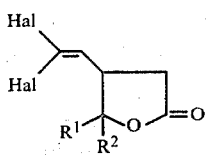

with a chlorinating agent selected from the group consisting of thionyl chloride and phosgene and then with an alcohol of the formula $R^4$—OH.

3. A process according to claim 2, in which the chlorination is effected between about 50° and 150° C.

4. A process according to claim 2, in which the chlorination is effected in the presence of an inert solvent selected from the group consisting of a hydrocarbon, chlorohydrocarbon or ether.

5. A process according to claim 2, in which the alcohol $R^4$—OH is reacted at between about 0° and 80° C.

6. A process according to claim 2, in which the reaction with the alcohol $R^4$—OH is accelerated in the presence of a tertiary amine as catalyst.

7. A process according to claim 1, in which the reaction is effected between about −20° and 120° C.

8. A process according to claim 1, in which the base is an aqueous solution of sodium hydroxide or potassium hydroxide.

9. A process according to claim 1, in which A, B, C and D each independently is alkyl with 1–18 carbon atoms, benzyl, benzyl substituted by $C_1$–$C_4$-alkyl, methoxy or halogen, phenyl or phenyl substituted by $C_1$–$C_4$-alkyl, $C_{1-4}$-alkoxy or halogen.

10. A process according to claim 1, in which $R^1$ and $R^2$ each independently is $C_{1-4}$-alkyl, Hal is chlorine or bromine, and $R^3$ is a benzyl, α- or β-naphthylmethyl, furylmethyl or benzofurylmethyl radical, which is optionally substituted in the aromatic ring or at the α-carbon atom by halogen, CN, alkyl with 1–4 carbon atoms, halogenoalkyl with 1–4 carbon atoms and 1–5 halogen atoms, or by aryl, hetero-aryl or aryloxy which is itself optionally substituted by halogen or by halogenoalkoxy or halogenoalkylmercapto with in each case 1–4 carbon atoms and up to 5 halogen atoms.

11. A process according to claim 1, in which $R^1$ and $R^2$ each is methyl.

12. A process according to claim 1, in which $R^3$ is 3-phenoxybenzyl, 3-phenoxy-α-cyanobenzyl or pentahalogenobenzyl.

13. A process according to claim 2, in which $R^1$ and $R^2$ each is methyl, and $R^3$ and $R^4$ each is 3-phenoxybenzyl, 3-phenoxy-α-cyanobenzyl or pentahalogenobenzyl, the chlorinating agent is thionyl chloride or phosgene, chlorination is effected between about 70° and 110° C. in the presence of an inert solvent selected from the group consisting of a hydrocarbon, chlorohydrocarbon or ether, the reaction with the alcohol is effected between about 20° and 50° C. in the presence of a tertiary amine as catalyst, the base is an aqueous solution of sodium hydroxide or potassium hydroxide and the reaction with the base is effected in the presence of about 0.3 to 6% by weight of the butanecarboxylic acid ester of tetraethylammonium chloride, tetrabutylammonium chloride, tetrabutylammonium bromide, tetrabutylphosphonium chloride, benzyltriethylammonium chloride, phenylbenzyldimethylammonium chloride, benzyldodecyldimethylammonium chloride or benzyltributylammonium chloride as catalyst.

* * * * *